「(12) United States Patent
Schirrmeister et al.

US009421513B2

(10) Patent No.: US 9,421,513 B2
(45) Date of Patent: Aug. 23, 2016

(54) CATALYST-COATED SUPPORT, METHOD FOR THE PRODUCTION THEREOF, A REACTOR EQUIPPED THEREWITH, AND USE THEREOF

(75) Inventors: Steffen Schirrmeister, Mühlheim an der Ruhr (DE); Martin Schmitz-Niederau, Münster (DE); Ingo Klüppel, Schwerte (DE); Christoph Filthaut, Dortmund (DE)

(73) Assignee: THYSSENKRUPP UHDE GMBH, Dortmund (DE)

( * ) Notice: Subject to any disclaimer, the term of this patent is extended or adjusted under 35 U.S.C. 154(b) by 1235 days.

(21) Appl. No.: 13/380,142

(22) PCT Filed: Jun. 23, 2010

(86) PCT No.: PCT/EP2010/003770
§ 371 (c)(1),
(2), (4) Date: Feb. 17, 2012

(87) PCT Pub. No.: WO2011/000493
PCT Pub. Date: Jan. 6, 2011

(65) Prior Publication Data
US 2012/0198769 A1 Aug. 9, 2012

(30) Foreign Application Priority Data
Jun. 30, 2009 (DE) ........................ 10 2009 031 305

(51) Int. Cl.
*B01J 12/00* (2006.01)
*B01J 19/00* (2006.01)
*B01J 21/08* (2006.01)
*B01J 19/24* (2006.01)
*B01J 23/52* (2006.01)
*B01J 35/10* (2006.01)
*B01J 37/02* (2006.01)
*B01J 37/34* (2006.01)
*C07C 45/35* (2006.01)
*C07C 51/215* (2006.01)
*C07C 67/05* (2006.01)
*B01D 53/86* (2006.01)
*B01J 23/66* (2006.01)
*B01J 35/00* (2006.01)
*B01J 37/00* (2006.01)

(52) U.S. Cl.
CPC ............ *B01J 19/249* (2013.01); *B01J 12/007* (2013.01); *B01J 19/0093* (2013.01); *B01J 21/08* (2013.01); *B01J 23/52* (2013.01); *B01J 35/10* (2013.01); *B01J 37/0217* (2013.01); *B01J 37/0225* (2013.01); *B01J 37/0232* (2013.01); *B01J 37/0244* (2013.01); *B01J 37/349* (2013.01); *C07C 45/35* (2013.01); *C07C 51/215* (2013.01); *C07C 67/05* (2013.01); *B01D 53/86* (2013.01); *B01D 2257/7022* (2013.01); *B01J 23/66* (2013.01); *B01J 35/006* (2013.01); *B01J 35/1066* (2013.01); *B01J 37/0045* (2013.01); *B01J 2219/0086* (2013.01); *B01J 2219/00783* (2013.01); *B01J 2219/00788* (2013.01); *B01J 2219/00822* (2013.01); *B01J 2219/00824* (2013.01); *B01J 2219/00835* (2013.01); *B01J 2219/00837* (2013.01); *B01J 2219/00846* (2013.01); *B01J 2219/2453* (2013.01); *B01J 2219/2458* (2013.01); *B01J 2219/2459* (2013.01); *B01J 2219/2479* (2013.01)

(58) Field of Classification Search
CPC ..... C07C 45/35; C07C 47/22; C07C 51/215; C07C 53/08; C07C 67/05; C07C 69/15; B01J 12/007; B01J 19/0093; B01J 19/249; B01J 21/08; B01J 23/52; B01J 35/10; B01J 37/0217; B01J 37/0225; B01J 37/0232; B01J 37/0244; B01J 37/349
See application file for complete search history.

(56) References Cited

U.S. PATENT DOCUMENTS

| 7,981,830 | B2 | 7/2011 | Schirmeister et al. |
| 2005/0129603 | A1 | 6/2005 | Szillat et al. |
| 2006/0183636 | A1 | 8/2006 | Klein et al. |
| 2007/0238605 | A1 | 10/2007 | Strehlau et al. |
| 2008/0160250 | A1 | 7/2008 | Adler et al. |
| 2008/0286176 | A1* | 11/2008 | Schirmeister et al. ....... 422/198 |
| 2009/0036557 | A1 | 2/2009 | Ratke et al. |

FOREIGN PATENT DOCUMENTS

| DE | 2237354 A1 | 2/1974 |
| DE | 2951577 A1 | 7/1981 |
| DE | 42 25 106 | 2/1994 ............ A61C 13/02 |
| DE | 19523382 A1 | 1/1997 |

(Continued)

OTHER PUBLICATIONS

International Preliminary Report on Patentability, Dec. 31, 2011.
(Continued)

*Primary Examiner* — Colleen Dunn
(74) *Attorney, Agent, or Firm* — Michael W. Ferrell; Ferrells, PLLC; Anna L. Kinney

(57) ABSTRACT

A catalyst-coated support including a sheetlike support, a primer layer applied thereto and composed of nanoparticles composed of silicon oxide-comprising material, and at least one catalyst layer applied to the primer layer. The layers applied are notable for a particularly good adhesive bond strength and can be used particularly efficiently in heterogeneously catalyzed gas phase reactions, especially in microreactors.

15 Claims, No Drawings

(56) References Cited

FOREIGN PATENT DOCUMENTS

| | | | |
|---|---|---|---|
| DE | 19719395 A1 | 11/1998 | |
| DE | 198 39 782 | 3/2000 | ................ B01J 8/06 |
| DE | 199 04 692 | 8/2000 | ............ B01D 53/75 |
| DE | 19911477 A1 | 9/2000 | |
| DE | 4334410 C3 | 5/2002 | |
| DE | 695 23 684 | 8/2002 | ............ B01C 53/94 |
| DE | 10211958 A1 | 10/2003 | |
| DE | 10216464 A1 | 10/2003 | |
| DE | 10357539 A1 | 7/2005 | |
| DE | 10 2004 048 974 | 4/2006 | ............ B01J 23/62 |
| DE | 102004048974 A1 | 4/2006 | |
| DE | 10 2005 019 000 | 10/2006 | ............ B01J 35/10 |
| DE | 102005019000 A1 | 10/2006 | |
| DE | 10 2005 038 612 | 2/2007 | ............ B01D 69/12 |
| DE | 603 08 698 | 8/2007 | ............ B01J 19/00 |
| DE | 102006036498 A1 | 2/2008 | |
| DE | 102006046553 A1 | 4/2008 | |
| EP | 0 246 413 | 11/1987 | ............ B01D 53/36 |
| EP | 1 287 886 | 3/2003 | ............ B01J 21/08 |
| EP | 1287886 A1 | 3/2003 | |
| EP | 1 514 846 | 3/2005 | ........... C01G 23/047 |
| EP | 1514846 A1 | 3/2005 | |
| EP | 1 825 352 | 5/2008 | ............ B01J 23/42 |
| WO | 96/22942 | 8/1996 | ............ C01B 33/16 |
| WO | 96/26890 | 9/1996 | |
| WO | 2008/021232 | 2/2008 | ............ H01M 8/24 |
| WO | 2008021232 A2 | 2/2008 | |

OTHER PUBLICATIONS

Datenblatt, PYROSIL® Flammenbeschichtungsgerät GVE, Sura Instruments, GmbH.

Das Pyrosil®—Verfahren, Technologie zur Erzeugung, haftvervessemder Oberflächen, Sura Instruments GmbH (relevant to PYROSIL® CCVD process).

SurA Handbeflammungsgeräte FB 07 & FB 25, Apr. 2003, Sura Instruments GmbH (relevant to PYROSIL® CCVD process).

Von Roland Weidl et al., Dünnschicht-/ Plasmatechnik, "Atmosphärendruck C-CVD Beschichtungs-vertahren—Trends und Entwicklungen", Galvanotechnik, 2007, pp. 1978-1982, Issue 8, Leuze Verlag (relevant to C-CVD process).

Deutsche Bundesstiftung Umwelt, Wir fördem Innovationen!, Silikat-Schichten zur Vorbehandlung von Oberflächen, Jul. 6, 2008, Sura Instruments GmbH (relevant to PYROSIL® CCVD process).

Datenblatt, PYROSIL® Flammenbeschichtungsgerät GVE, Sura Instruments, GmbH (relevant to PYROSIL® CCVD process).

Corresponding European Office Action dated Jan. 15, 2016.

* cited by examiner

CATALYST-COATED SUPPORT, METHOD FOR THE PRODUCTION THEREOF, A REACTOR EQUIPPED THEREWITH, AND USE THEREOF

CLAIM FOR PRIORITY

This application is based on International Application No. PCT/EP2010/003770, filed Jun. 23, 2010 which was based on German Patent Application No. 10 2009 031 305.2, filed Jun. 30, 2009. The priorities of the foregoing applications are hereby claimed and their disclosures incorporated by reference.

TECHNICAL FIELD

The present invention relates to a catalyst-coated support, and also to a process for preparation thereof and to a reactor comprising this support.

BACKGROUND

Supported catalysts are used on a large scale in different fields of industry. In addition to catalysts which have been applied to finely divided support materials, catalyst layers applied to sheetlike supports have also already been described.

DE 198 39 782 A1 describes metallic reaction tubes with catalytic coating. The coating is a multimetal oxide material comprising molybdenum and bismuth, which is applied directly to the reaction tube. There are no adhesion-promoting intermediate layers.

DE 199 04 692 A1 describes a structured adsorber system for removal of pollutants with low concentration from process gases, waste air or ambient air. This system comprises an adsorptive layer applied to a support and at least one catalyst layer; in this case, a temperature varying with time is imposed along the flow direction on at least one adsorption layer in the phase of desorption. What is described is a metallic support which has, on the surface, an oxidic adhesive layer to which the adsorbent or the catalyst has been applied. The material specified for an oxidic adhesive layer is aluminum oxide.

DE 603 08 698 T2 describes a microchannel reactor with bound catalyst. One of the examples discloses a silica-coated aluminum plate. This coated surface is chemically modified with a solution of N,N-dimethylpropylaminotrimethoxysilane, and used as a catalyst for the Michael addition of methyl vinyl ketone and nitroethane to give 5-nitrohexan-2-one. The use of adhesion-improving layers is not described.

DE 695 23 684 T2 describes a catalyst for cleaning of automotive exhaust gases. This catalyst consists of a support and two catalyst layers applied thereto. Intermediate layers for improving adhesion are not disclosed.

DE 10 2005 038 612 A1 discloses a process for producing membranes coated with catalyst on both sides for use in electrochemical devices. This involves producing two semifinished parts by applying an ionomer layer to a support in each case, and applying an anode catalyst layer or a cathode catalyst layer thereto. After the drying of the catalyst layers, the particular supports are removed and the two ionomer layers are bonded to one another so as to form a membrane which has an anode catalyst layer and a cathode catalyst layer.

DE 10 2005 019 000 A1 describes catalytically coated supports with porous catalyst layers, and catalyst layers comprising cavities. These are notable for high adhesive bond strengths. This document also describes the possibility of using an adhesion promoter layer between substrate and catalyst layer; the thickness thereof is typically 100 nm to 80 μm, and the layer is formed from materials which do not have any individual structures of diameter more than 5 μm. Further details of the nature of this adhesion promoter layer are not to be found in the document.

EP 0 246 413 A1 describes a plate-shaped catalyst for reducing the level of nitrogen oxides in flue gases. To improve the adhesion between support plate and catalyst material, an intermediate layer of ceramic material is provided, which has been applied by plasma spraying or by flame spraying. The sole example of a ceramic material mentioned in this document is titanium dioxide.

DE 10 2004 048 974 A1 describes an oxidation catalyst for the removal of pollutants from oxygen-rich off-gases and a process for its manufacture. The catalyst comprises tin oxide, palladium and a carrier oxide, wherein said carrier oxide is a nanoparticulate material. Thus a catalyst is disclosed comprising selected active materials which are deposited on a nanoparticulate oxide. From these catalysts deposited on a carrier mouldings can be formed, for example, or these catalysts can be used to coat a honeycomb material. The nanoparticulate oxide can be manufactured, among others, by using flame pyrolysis. A deposition of catalytically active materials on a sheet-like carrier equipped with a primer layer is not disclosed.

It is known that, for improving the adhesion of organic coatings, for example of lacquers, silicon oxide layers applied by plasma spraying, especially by flame spraying, are advantageous. Such processes are known, for example, as CCVD processes ("combustion chemical vapor deposition"). One example thereof is the Pyrosil® process, which is already being used commercially to obtain adhesion-improving surfaces.

In the field of dental prostheses, processes for producing metal-plastic bonds are known. For instance, DE patent 34 03 894 describes the production of a metal-plastic bond by the "Silicoater process". This involves applying a thin, glasslike $SiO_x$—C layer to a sandblasted metal surface by means of a flame hydrolysis burner, then applying an activated adhesive silane, sealing the surface thus formed with an opaque layer and then applying a plastic to this layer. DE 42 25 106 A1 discloses a further process for producing metal-plastic bonds, in which an adhesion-promoting oxide layer is formed on a metallic part and is then bonded to a plastic via an intermediate layer composed of an adhesive silane. The adhesion-promoting oxide layer is generated by decomposition of an organosilicon or organometallic compound in a spark gap.

Proceeding from this prior art, it is an object of the present invention to provide a catalyst-coated support which is notable for excellent adhesion of the catalyst layers.

The invention further provides an easily performable process for coating of sheetlike supports with catalysts, which works with readily obtainable and inexpensive materials and is therefore economically advantageous.

SUMMARY OF INVENTION

It has now been found that, surprisingly, primer layers comprising oxidic silicon nanoparticles are outstandingly suitable for improving the adhesion of catalyst layers to sheetlike supports. These primer layers can be applied by CCVD processes known per se.

The present invention relates to a catalyst-coated support comprising a sheetlike support, a primer layer applied thereto and comprising nanoparticles of silicon oxide-comprising material, and at least one catalyst layer applied to the primer layer.

Details, advantages and various embodiments of the invention are described below.

DETAILED DESCRIPTION OF INVENTION

The invention is described in detail below with reference to several embodiments and numerous examples. Such discussion is for purposes of illustration only. Modifications to examples within the spirit and scope of the present invention, set forth in the appended claims, will be readily apparent to one of skill in the art. Terminology used throughout the specification and claims herein is given its ordinary meaning. Terminology is further defined below.

In the context of the present description, "sheetlike support" is understood to mean a support which has one or more surfaces of area at least 1 mm². In contrast to finely divided supports, sheetlike supports are thus characterized by the presence of at least one surface with macroscopic dimensions. The sheetlike supports used in accordance with the invention may have any desired geometries and may consist of a wide variety of different materials. For example, the structures may be tubes, plates or other kinds of structures, which may form either reactor walls or reactor internals. Preference is given to using sheetlike bodies which have two-dimensional depressions to which the catalyst layers are applied.

The sheetlike support preferably consists of metallic or ceramic materials. For example, the sheetlike support may consist of an aluminum-, iron-, copper- or nickel-containing metal, or of a metal alloy; or it may consist of ceramics, for example of aluminum oxide, titanium oxide or silicon oxide, silicon carbide or cordierite.

The surface of the sheetlike support may be as desired. In addition to smooth surfaces, it is possible to use roughened or porous surfaces. The surface may consist of the material of the support or have an oxide layer.

Preferably, the surface of the sheetlike support is smooth and the sheetlike support has been rolled or punched or imprinted. Moreover, sheetlike supports with a milled surface are used with preference.

According to the invention, an adhesion-promoting layer of a selected silicon oxide-comprising material has been applied to at least one of the surfaces of the sheetlike support. Typical thicknesses of this adhesion-promoting layer are less than 100 nm, preferably 20 to 100 nm, most preferably 30 to 50 nm.

The adhesion-promoting layer is essentially formed from nanoparticulate particles. These may occur as noncoherent units on the surface as individual particles or in the form of aggregates on the surface, or these particles form a coherent layer of nanoparticulate particles. The shape and size of the individual nanoparticulate particles may vary within wide ranges. In addition to round or rotationally symmetric particles, irregular particle forms are also possible. The diameter of the particles varies typically within the range from 5 to 50 nm. The adhesion-promoting layer thus exhibits a substantially homogeneous matrix within the micrometer range.

The silicon oxide-comprising materials which form the base material of the adhesion-promoting layer may have different chemical compositions. This layer may be hydrophobic or else hydrophilic.

The compounds which build up the adhesion-promoting layer can be synthesized by decomposition of organic or inorganic silicon compounds in thermal or nonthermal plasma. It is also possible to pyrolyze layers of hydrophobic inorganic aerogels in the presence of oxygen, as described, for example, in WO-A-96/26,890. In addition, it is also possible to apply silicatic layers to the sheetlike support, by introducing vapors or aerosols of silicon compounds into an oven which contains the support to be coated in a preferably inert atmosphere, in which case a silicon-containing layer is deposited on the support. This process is described in DE 10 2006 046 553 A1. Moreover, the materials used to build up the adhesion-promoting layer may be $SiO_2$ aerogels comprising carbon particles. These are described, for example, in DE 43 00 598 A1.

Particular preference is given to applying the adhesion-promoting layer to the sheetlike support by plasma spraying, especially by flame spraying, of silicon compounds in an oxidizing atmosphere.

Usable silicon compounds, which can be used especially in flame or plasma spraying, are any desired silicon compounds, provided that they can be sprayed into a flame or a plasma. In addition to silicon aerogels, preference is given to using pyrolyzable silicon compounds. More preferably, silicon compounds soluble in water or organic solvents, or silicon compounds evaporable at flame or plasma temperatures, are usable. These include especially silicon-hydrogen compounds, silicon-carbon compounds or water-soluble silicates.

Examples of silicon-hydrogen compounds are silanes such as compounds with the formula $Si_aH_{2a-b+2}R_b$ in which R is a monovalent organic radical or a halogen atom, a is an integer from 1 to 20 and b is an integer from 0 to 19.

Examples of silicon-carbon compounds are organosilanes, such as compounds with the formula $Si_aR'_{2a+2}$ in which R' may have different meanings within one molecule and is a monovalent organic radical, preferably an alkyl and/or alkoxy group, and a is an integer from 1 to 20.

Examples of water-soluble silicates are waterglasses, for example sodium waterglass, ammonium waterglass or potassium waterglass.

Apparatus for plasma spraying or for flame spraying is known and commercially available. It is possible to use apparatus for generation of nonthermal plasma, microwave plasma generators, and apparatus for generation of thermal plasmas, for example flames. The process can be conducted within or preferably outside the plasma source.

The silicon compounds are introduced into the plasma, preferably in the form of a flame, for example in the form of an atomized liquid or in vapor form. The plasma or flame spraying is effected preferably in an oxidizing atmosphere, especially in air. Under these conditions, the pyrolyzable silicon compound decomposes and forms silicon oxide-comprising products which are precipitated in the form of nanoparticles or of aggregates of nanoparticles on the surface of the sheetlike support. The application of a nanoparticulate surface layer of silicon oxide achieves surface silicatization. This can be achieved by the above-described feeding of an organosilicon compound into a flame. This treatment generates a thin, but very dense and firmly adhering silicon oxide layer with high surface energy on the support surface. This layer adheres virtually to all surfaces and forms a nanoporous surface structure which ensures firstly better mechanical anchoring of the layers applied subsequently and secondly optimal chemical attachment of components of the subsequent layers to the silicate layer. Additional coating of the nanoporous silicon oxide layer with adhesion promoters allows a further improvement of the catalyst layer to be achieved.

For the flame spraying, the pyrolysis gas used may be a butane gas or propane gas or a mixture of the two gases together with a silane and/or a silane-carbon compound. For instance, the silane and/or the silane-carbon compound can be fed into a propane-butane gas flame. In the reducing part of the flame, in the core flame, the hydrocarbons and the silane and/or the silane-carbon compound are combusted. In the oxidizing, outer part of the flame, the silane fragments formed are deposited on the surface as a high-energy silicate layer. To this end, the surface to be coated is preferably treated with the oxidizing part of the flame briefly and with constant movement of the burner.

The thickness and structure of the primer layer which forms can be adjusted by the person skilled in the art by adjusting process parameters, such as distance of the flame or of the plasma from the surface, and also the treatment time or the concentration of the pyrolyzable material in the flame or the plasma.

The primer layer applied in accordance with the invention comprises, as the base material, silicon oxide, preferably a material of the formula $SiO_x$ in which x is a rational number of less than or equal to 2, especially between 1 and 2. In addition to silicon and oxygen, the primer layer may also contain other elements, for example halogen, nitrogen, carbon or metals, such as alkali metals in the form of alkali metal ions.

At least one layer of catalytically active material has been applied to the primer layer; this layer preferably has pores, especially structures with a diameter of more than 1 μm. In addition to micropores with diameters of less than 1 μm, this layer also contains macropores with diameters of at least 1 μm.

The catalyst layer typically contains structures which originate from particles with a diameter of more than 1 μm; the catalyst layer comprises catalytically active material and possibly of further, inert material. It is also possible for a plurality of catalytically active layers to be applied to the primer layer.

The porous catalyst layer more preferably contains cavities. Cavities are understood in the context of the present description to mean irregular cavities with dimensions of greater than 5 μm in at least two dimensions or with cross-sectional areas of at least 10 μm².

These cavities in these preferred catalyst layers are essentially closed and are essentially joined to the layer surface or further cavities only by pores with diameters of less than 5 μm or cracks with a width of less than 5 μm. Cavities can be identified in section images from scanning electron micrographs of resin-impregnated catalyst layers.

The cross-sectional area or the dimensions can be determined by processes known per se, for example by quantitative microscopy. Irregular cavities are understood in the context of this description to mean cavities with aspherical and/or acylindrical geometry deviating significantly from the ideal spherical and/or cylindrical form, the inner surface of which consists of local roughness and macropores. In contrast to cracks, cavities have no clear preferential direction.

Cavities are a constituent of the pore system of these preferred catalyst layers. These are particularly large macropores. According to the IUPAC definition, macropores are pores having a diameter of greater than 50 nm.

The presence of cavities in the catalyst layer imparts another additional increase in the adhesive bond strengths to the coated support, even after mechanical or thermal stress.

In addition to the cavities, the catalyst layer used with preference in accordance with the invention preferably has further macropores of smaller diameter in a high proportion.

In a particularly preferred embodiment, the catalyst layer contains a pore system in which at least 50%, preferably at least 70%, of the pore volume is formed by macropores with a diameter of least 50 nm. Pore volume is understood to mean the volume, detectable by means of mercury porosimetry according to test method DIN 66133, in pores with a diameter of greater than 4 nm. A contact angle of 140° and a surface tension of 480 mN/m for mercury are assumed. Before the measurement, the sample is dried at 105° C. The proportion of the pore volume in macropores is likewise determined by mercury porosimetry.

The combined pore and cavity volume of the preferred catalyst layer, which can be determined by saturating water absorption and difference weighing, is typically 30 to 95%, preferably 50 to 90%, based on the total volume of the layer.

The thickness of the catalyst layer or of the catalyst layers is not subject to any particular restrictions. Typically, the thickness of the porous catalyst layers is selected such that reactants can diffuse under the reaction conditions from the outer surface of the catalyst layer as far as the support substrate; the thicknesses are preferably up to 3 mm, for example between 50 μm and 2.5 mm, preferably between 100 μm and 1.5 mm. Thick catalyst layers ensure the best possible exploitation of the catalyst per unit area of coated surface.

The catalytic materials can be selected from a wide range. Of particular interest are catalyst systems for strongly exo- or endothermic reactions, especially for oxidation reactions. Examples of base systems which can be varied with promoters include:

metal catalysts, such as stainless steel, molybdenum or tungsten catalysts, noble metal catalysts, such as platinum, palladium, rhodium, rhenium, gold and/or silver catalysts, which may be supported, for example, on ceramic or activated carbon, multimetal oxide catalysts, which, as the base structure, as well as further dopants, consist of a selection of the oxides of molybdenum, of bismuth, of vanadium, of tungsten, of phosphorus, of antimony, of iron, of nickel, of cobalt and of copper, zeolite catalysts, for example molecular sieves based on titanium-containing molecular sieves of the general formula $(SiO_2)_{1-x}(TiO_2)_x$, such as titanium silicalite-1 (TS1) with MFI crystal structure, titanium silicalite-2 (TS-2) with MEL crystal structure, titanium beta-zeolite with BEA crystal structure, and titanium silicalite-48 with the crystal structure of zeolite ZSM 48, Fischer-Tropsch catalysts, especially based on Co or Fe, Fe-, Ni-, Co- or Cu-based catalysts, solid bases or acids, mixtures of these systems.

Particular preference is given to using the following catalyst systems:

titanium silicalite-1

Pd, Au and potassium acetate on an oxidic support, preferably on an oxide with a high silicon oxide content mixtures of the oxides and mixed oxides of Mo, Bi, Fe, Co, Ni and optionally further additions, e.g. K mixtures of the oxides and mixed oxides of Mo, V, Cu, W and optionally further additions, e.g. Sb, Nb Ag on an aluminum oxide which is preferably at least partly in the alpha phase, and optionally further additions, e.g. Cs, Re vanadium pyrophosphates and optionally further additions Pd and/or Pt, optionally combined with tin on aluminum oxide The catalytically active materials may be present in an inert or supporting matrix composed of inorganic oxides or thermally stable polymers. Preferred materials of this matrix are oxides of Si, Al, Ti, Zr and/or mixtures thereof.

In addition, further doping elements and other secondary components customary for preparation of catalyst layers may be present in each case. Examples of such materials are alkali metal and alkaline earth metal compounds.

The catalytically active layers more preferably comprise, as well as the catalytically active material, binders composed of oxygen compounds of silicon, especially of silicatic material. These binders, together with the material of the primer layer, give rise to particularly high adhesive bond strengths.

The catalyst materials used may be all catalysts usable for the reaction envisaged.

The supports coated in accordance with the invention can be used for a wide variety of different heterogeneously catalyzed reactions in the liquid phase and especially in the gas phase.

Examples of reactions are oxidation, hydrogenation or ammoxidation reactions, such as the catalytic oxidation of olefins, preferably the catalytic epoxidation of olefins, the catalytic oxidation of olefins to aldehydes and/or carboxylic acids, the catalytic hydrogenation of organic compounds or the complete or partial oxidation of a hydrocarbon-containing gas mixture, especially the preparation of synthesis gas, the oxidative dehydrogenation of hydrocarbons or the oxidative coupling of hydrocarbons.

Examples of the epoxidation of ethylenically unsaturated compounds are the oxidation of propene to propene oxide, or of ethylene to ethylene oxide; an example of the oxidative coupling of hydrocarbons is the coupling of acetic acid and ethylene to give vinyl acetate; examples of oxidation reactions are the oxidation of ethane to acetic acid or the oxidation of propene to acrolein or acrylic acid. Further examples of reactions are hydrogenation reactions, for example the selective hydrogenation of unsaturated organic compounds.

The invention also relates to the use of the catalytically coated supports for these purposes.

Examples of catalytically active materials which may be present in the catalyst layer are catalytically active metals, semimetals including alloys, oxidic materials, sulfidic materials and silicatic materials.

The inventive supported catalyst layer systems have high adhesive bond strengths. These layer systems typically exhibit adhesive bond strengths of >1 kPa (measured based on DIN EN ISO 4624), especially >10 kPa and very particularly >50 kPa.

Particular preference is given to sheetlike supports with catalytic coating, a thickness of the catalytically active layer of >50 µm, preferably 50 µm to 2.5 mm, most preferably 100 µm to 1.5 mm, and an adhesive bond strength of the layer of >10 kPa.

The inventive support with catalytic coating can be prepared by a particularly simple and economic process. This likewise forms part of the subject matter of the present invention.

The invention therefore also relates to a process for preparing a catalyst-coated support, comprising the measures of:
i) coating at least one surface of a sheetlike support with a primer layer composed of nanoparticles composed of silicon oxide-comprising material, by
ii) applying at least one silicon compound in an oxidizing atmosphere in the presence of a thermal or nonthermal plasma to the surface of the sheetlike support, and
iii) applying at least one layer comprising catalytically active constituents or precursors thereof to the support provided with the primer layer.

Particular preference is given to coating the sheetlike support with the primer layer by plasma spraying, very particularly by flame spraying, of silicon-hydrogen compounds, silicon-carbon compounds or aqueous solutions of water-soluble silicates in an oxidizing atmosphere.

Very particular preference is given to using silanes and/or silane-carbon compounds as the silicon compound.

The flame or plasma temperature in the course of flame or plasma spraying is selected such that the pyrolyzable silicon compound decomposes under the conditions of application. Typically, temperatures of at least 500° C. are used, preferably between 500° C. and 2000° C.

For the flame spraying process, it is possible to use commercial one- or two-substance nozzles, in which case the nozzle is supplied with a combustible mixture and the silicon compound. The combustible mixture used may, for example, be a mixture of hydrocarbons and air, for example a propane-air mixture. The pyrolyzable silicon compound is sprayed into the flame or is already present in the combustible mixture. The flame can be guided over the surface manually or preferably in an automated manner. In the automated method, it is advisable to move the nozzle under computer control over the surface to be sprayed, and in doing so to monitor and adjust the application of the material and further process parameters in a controlled manner.

The primer layer can be sprayed on in a manner known per se, for which a multitude of process parameters are available to the person skilled in the art. Examples thereof are the spray pressure, the spray distance, the spray angle, the advance rate of the spray nozzle, or of the substrate in the case of a fixed spray nozzle, the nozzle diameter, the material flow rate, the geometry of the spray jet, the flame temperature and the concentration of the pyrolyzable silicon compound in the flame.

Alternatively to a flame, the pyrolyzable silicon compound can also be sprayed in another plasma which can be generated, for example, by microwaves.

The catalytically active layer(s) can be applied by processes known per se, for example by knife coating, painting or especially by spraying.

Preference is given to spraying on a suspension with solids content at least 40% by weight, comprising particles of catalytically active material with a mean diameter ($D_{50}$) of at least 5 µm and/or precursor thereof, and optionally further constituents of catalytically active layers, and this step may be repeated once or more than once.

In a further preferred embodiment, the particles of the suspension have a rough surface and irregular shape, as is the result, for example, of grinding or crushing.

In a further preferred embodiment, a binder is added to the suspension. Suitable binders are especially brine, very finely divided suspensions or solutions of the oxides of Al, Si, Ti, Zr or mixtures thereof, most preferably brine or solutions of silicon oxides.

In a further variant of the process according to the invention, a suspension with solids content at least 40% by weight, comprising particles of inert material with a mean diameter ($D_{50}$) of at least 5 µm and optionally further constituents of catalytically reactive layers is sprayed on, and this step may be repeated once or more than once. Subsequently, the layer system, after preparation thereof, is impregnated with a catalytically active material and/or precursor thereof.

After the application of the individual layers or of the overall layer system or parts thereof, they can optionally be dried and/or calcined, before further treatments of the layers.

A calcination, for example at a temperature of 250 to 1200° C., can be used to remove organic or other decomposable residues. The pretreatment may consist in a combination of these individual processes, the sequence of which is variable.

The catalyst suspension applied comprises at least one or more than one catalytically active material(s) or precursor(s) thereof.

Precursors may, for example, be nitrates, oxalates, carbonates, acetates or other salts, which can be converted to oxides, for example, by thermal or oxidative decomposition.

The catalytically active materials or precursors thereof may be present in molecular, colloidal, crystalline or/and amorphous forms. The actual catalytic materials, or precursors thereof, may be present in the suspension or may be applied later by impregnation.

To adjust the pH, acids or bases can be added. In addition, organic constituents such as surfactants, binders or pore formers may be present. A suitable suspension medium or solvent is especially water. However, it is also possible to use organic liquids.

This suspension to be applied can be applied by means of spraying. Parts which are not to be wetted can be covered or masked.

For the spraying process, it is possible to use commercial one- or two-substance nozzles, and the jet can be guided manually or preferably in an automated manner. In the automated method, it is advisable to move the nozzle under computer control over the surface to be sprayed and in doing so to monitor and adjust the application of the material and further process parameters in a controlled manner.

The individual layers can be sprayed on in a manner known per se, for which a multitude of process parameters are available to the person skilled in the art. Examples thereof are the spray pressure, the spray distance, the spray angle, the advance rate of the spray nozzle, or of the substrate in the case of a fixed spray nozzle, the nozzle diameter, the material flow rate and the geometry of the spray jet. In addition, the properties of the suspensions to be sprayed can exert an influence on the quality of the resulting layers, for example density, dynamic viscosity, surface tension and zeta potential of the suspension used.

To prepare the support coated in accordance with the invention, a layer by layer application can be effected, which is preferably repeated once or more than once.

The application of the particular layer may be followed by one or two thermal treatments for drying and calcination. If the layer applied has not already been dried, a separate drying can be effected, for example at temperatures of 20-200° C., or drying in combination with a calcination, for example at temperatures of 200-1000° C. The drying and the calcination can be performed in an oxidizing atmosphere, for example in air, or in an inert atmosphere, for example in nitrogen.

It is also possible first to apply all layers and then to dry and to calcine the layer system.

In the case of spray application of more than one layer comprising catalytically active material, these layers may have the same composition, i.e. the same second suspension is always used. However, it is also possible to obtain layers comprising catalytically active material with different composition or some layers consisting of inert material.

In order to smooth the layers applied, the surface of the layer system obtained can be ground or, for example, milled with CNC machines. It is possible with preference, even in the course of application of the individual layers, to obtain very substantially planar layers with low tolerance of the total layer thickness of less than ±25 µm, such that no further processing is necessary.

After the drying or calcination, it is optionally possible to apply further catalytic components, or precursors thereof, by impregnation. For reasons relating to occupational hygiene and economics, it is generally advisable also to perform such an impregnation only after any mechanical final treatment. To this end, the support layer is coated with the solution or suspension comprising the components or immersed into it, or else sprayed. The impregnation may be followed by a drying and/or a calcination.

The supports coated in accordance with the invention can be used in a wide variety of different reactors, for example in plate or tubular reactors.

The invention further provides a reactor comprising at least one of the inventive supports with catalytic coating.

Preference is given to using the inventive supports in wall reactors, which also include microreactors. In the context of this description, microreactors are understood to mean those reactors in which at least one of the dimensions of the reaction chamber or of the reaction chambers is less than 10 mm, preferably less than 1 mm, more preferably less than 0.5 mm.

Wall reactors and especially microreactors have several reaction chambers, preferably several reaction chambers parallel to one another.

The dimensions of the reaction chambers may be as desired, provided that at least one dimension is within the range of less than 10 mm.

The reaction chambers may have round, ellipsoidal, triangular or polygonal, especially rectangular or square, cross sections. One or more dimension(s) of the cross section is preferably less than 10 mm, i.e. at least one side length or the diameter.

In a particularly preferred embodiment, the cross section is rectangular or round and only one dimension of the cross section, i.e. one side length or the diameter, is within the range of less than 10 mm.

The material surrounding the reaction chamber may be any desired material, provided that it is stable under the reaction conditions, permits sufficient removal of heat, and the surface of the reaction chamber is fully or partly coated with the inventive layer system comprising catalytically active material.

The present invention thus also relates to a reactor which can be used especially for heterogeneously catalyzed gas phase reaction, wherein:
  a) there is at least one reaction chamber, of which at least one dimension is smaller than 10 mm, and
  b) the surface of the reaction chamber is coated or partly coated with the above-defined layer system composed of primer layer and layer(s) comprising catalytically active material.

A preferred microreactor has a multitude of vertical or horizontal and parallel chambers, each of which has at least one inlet and one outlet, the chambers being formed by stacked plates or layers, and some of the chambers being reaction chambers, of which at least one dimension is within the range of less than 10 mm, and the rest of the chambers being heat transfer chambers, the inlets to the reaction chambers being connected to at least two distributor units and the outlets from the reaction chambers being connected to at least one collecting unit, and the heat transfer between reaction and heat transfer chambers being effected through at least one common chamber wall which is formed by a common plate.

A microreactor of this type used with particular preference has spacer elements arranged in all chambers, contains catalyst material applied at least partly by the process according to the invention on the inner walls of the reaction chambers, has a hydraulic diameter which is defined as the quotient of four times the area to the peripheral length of the free flow cross section in the reaction chambers of less than 4000 µm, preferably less than 1500 µm and more preferably less than 500 µm, and a ratio between the vertically smallest distance of two adjacent spacer elements from the slot height of the reaction chamber after a coating with catalyst of less than 800 and greater than or equal to 10, preferably less than 450 and more preferably less than 100.

The invention still further provides for the use of the supports described in a reactor for conversion of organic compounds. The reactions may be in the gas phase, in the liquid phase or in the supercritical phase.

The invention is described in detail hereinafter by examples. This is not intended to impose a restriction.

EXAMPLES 1-4

Preparation of Catalyst Supports Coated with Nanoparticulate $SiO_2$ Layers

Hastalloy C-22 blanks with dimensions of 40×50 mm were provided with a nanoparticulate $SiO_2$ layer in a flame spraying system which worked by the Pyrosil® process. For the flame pyrolysis, propane gas was used, to which a small amount of an organosilicon compound (either tetramethylsilane or hexamethyldisiloxane) had been added. The samples were coated by repeatedly flaming the blank surface and by varying the distance between flame and blank surface. The distance was considered to be that between burner tip and blank surface. Before the coating, the blank surface was obtained by milling.

For example 1, the blank surface was conducted past the flame six times in succession at a distance of 10 mm each time.

For example 2, the blank surface was conducted past the flame six times in succession at a distance of 40 mm each time.

For example 3, the blank surface was conducted past the flame twelve times in succession at a distance of 10 mm each time.

For example 4, the blank surface was conducted past the flame twelve times in succession at a distance of 40 mm each time.

The wettability of the surfaces obtained in this way was tested by contact angle measurements. The contact angle measurements were carried out with a G2 contact angle measuring system (KRÜSS GmbH, Wissenschaftlicher Gerätebau Hamburg). To determine the contact angle, the sessile drop method was used. The measurement process employed was the measurement of the static contact angle. This involved placing a liquid droplet of deionized water of diameter 2 to 6 mm onto the surface of the catalyst plate and newly determining the contact angle repeatedly over a prolonged period. Within the diameter range employed, the contact angle to be measured is independent of the diameter of the droplet. The contact angle was measured immediately after the application of the droplet using a video system coupled to the contact angle measuring system, which recalls the profile of the liquid droplet applied, over a period up to approx. 20 seconds. The arithmetic mean of the eight measurements obtained was calculated.

The comparative example C1 employed was a rolled Hastalloy blank surface, 40×50 mm.

The results of the contact angle measurements after different storage times are reported in Table 1 below.

TABLE 1

| Example | Contact angle after preparation | Contact angle after storage for 4 days | Contact angle after storage for 8 days |
|---|---|---|---|
| 1 | 10.5° | 11.4° | 14.8° |
| 2 | 0° | 10° | 13° |
| 3 | 0° | 0° | 0° |
| 4 | 0° | 0° | 0° |
| C1 | 41° | 49° | 68° |

EXAMPLES 5-8

Preparation of Catalyst-Coated Samples

Hastalloy C-22 blanks with dimensions of 45×10×2 mm were coated analogously to examples 1-4 with nanoparticulate $SiO_2$ layers by flame spraying. Thereafter, catalyst layers were sprayed onto each of these blanks. The catalyst-coated samples corresponded to examples 5-8.

The catalyst used was a bentonite catalyst prepared with Pd and Au. For this purpose, a catalyst suspension consisting of 8.5 g of catalyst powder, 3.75 g of binder (Koestrosol 2040 AS) and 7.75 g of water was prepared. The sample blank was sprayed therewith, using an HS25 HVLP manual spray gun. The nozzle diameter was 1.8 mm, the spray pressure was 1.1 bar, the spray distance was 20 cm and the advance rate was 10 cm/sec.

As comparative example C2, an untreated Hastalloy sample was coated with catalyst under the aforementioned conditions.

To characterize the bond stability, a three-point micro bending test was carried out. For this purpose, the sample blanks were placed on their ends (clear distance: 40 mm) and a crossbeam was placed in the middle thereof. The bending stress was up to 2000 N, and the crossbeam was moved at a speed of 20 µm/sec. The bending of the sample blank at which the first crack formed in the catalyst layer and at which the base material lifted off was determined.

In addition, adhesive bond strength measurement was carried out to DIN EN ISO 4624.

The results of these tests are listed in Table 2 below.

TABLE 2

| Example | Adhesive bond strength (MPa) | Layer thickness (µm) | Bending 1st crack (mm) | Bending Lifting of base material (mm) | Flexural stress Lifting of base material (MPa) |
|---|---|---|---|---|---|
| 5 | 68.7 | 398 | 1.61 | 1.61 | 399 |
| 6 | 84.5 | 337 | 2.15 | 2.15 | 459 |
| 7 | 88.6 | 370 | 2.88 | 3.42 | 491 |
| 8 | 137.5 | 429 | 1.91 | 1.91 | 408 |
| C2 | 13.9 | 580 | 1.70 | 2.26 | 335 |

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

The invention claimed is:

1. A catalyst-coated support comprising a sheetlike support, a primer layer applied thereto by plasma spraying of silicon compounds in an oxidizing atmosphere and comprising nanoparticles of silicon oxide-comprising material, wherein the primer layer has a thickness of 20 to 100 nm, and at least one catalyst layer applied to the primer layer, wherein the at least one catalyst layer has a thickness of 50 μm to 3 mm.

2. The catalyst-coated support as claimed in claim 1, wherein the primer layer is a layer applied by flame spraying of silicon compounds in an oxidizing atmosphere.

3. The catalyst-coated support as claimed in claim 2, wherein the silicon compounds are silicon-hydrogen compounds, silicon-carbon compounds or water-soluble silicates.

4. The catalyst-coated support as claimed in claim 1, wherein the sheetlike support consists of metal or of ceramic.

5. The catalyst-coated support as claimed in claim 1, wherein the sheetlike support is configured in the form of a sheet, of a tube, of a reactor wall or of a reactor internal.

6. The catalyst-coated support as claimed in claim 1, wherein the surface of the sheetlike support has been milled, rolled, punched or imprinted.

7. The catalyst-coated support as claimed in claim 1, wherein the primer layer has a thickness of 30 to 50 nm.

8. The catalyst-coated support as claimed in claim 1, wherein the silicon oxide-comprising material is $SiO_x$ in which x is a rational number of less than or equal to 2.

9. The catalyst-coated support as claimed in claim 1, wherein the catalyst layer is porous and has such a thickness that reactants can diffuse from the surface down to the support substrate.

10. The catalyst-coated support as claimed in claim 9, wherein the catalyst layer contains cavities which are irregular cavities with dimensions of greater than 5 μm in at least two dimensions or with cross-sectional areas of at least 10 μm².

11. The catalyst-coated support as claimed in claim 10, wherein the catalyst layer contains a pore system in which at least 50% of the pore volume is formed by macropores having a diameter of at least 50 nm.

12. A reactor comprising at least one catalyst-coated support as claimed in claim 1.

13. The reactor as claimed in claim 12, which is a microreactor.

14. The reactor as claimed in claim 13, which is usable for heterogeneously catalyzed gas phase reaction and has at least one reaction chamber of which at least one dimension is smaller than 10 mm, at least one surface of the reaction chamber consisting of a coated support comprising a sheetlike support, a primer layer applied thereto by plasma spraying of silicon compounds in an oxidizing atmosphere and comprising nanoparticles of silicon oxide-comprising material, and at least one catalyst layer applied to the primer layer.

15. The reactor as claimed in claim 14, wherein the coated support is in the form of a tube, of a plate, of a reactor wall or of a reactor internal.

* * * * *